(12) United States Patent
Marik (10) Patent No.: US 8,097,022 B2
(45) Date of Patent: Jan. 17, 2012

(54) FLEXIBLE COUPLING MEMBERS FOR SPINAL STABILIZATION MEMBERS

(75) Inventor: Greg C. Marik, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1265 days.

(21) Appl. No.: 11/708,384

(22) Filed: Feb. 20, 2007

(65) Prior Publication Data

US 2008/0234743 A1   Sep. 25, 2008

(51) Int. Cl.
*A61B 17/70* (2006.01)

(52) U.S. Cl. ......... 606/260; 606/250; 606/257; 606/278

(58) Field of Classification Search .................. 606/246, 606/250–279; 403/301, 305, 306, 362
See application file for complete search history.

(56) References Cited

U.S. PATENT DOCUMENTS

| | | | | |
|---|---|---|---|---|
| 613,903 | A * | 11/1898 | Hussey | 403/180 |
| 1,753,041 | A * | 4/1930 | Bourdon | 245/1.5 |
| 1,959,402 | A * | 5/1934 | Anderson | 403/284 |
| 2,958,723 | A * | 11/1960 | Logan et al. | 174/84 C |
| 3,099,510 | A * | 7/1963 | Piorunneck | 439/851 |
| 3,281,524 | A * | 10/1966 | Lynch, Jr. et al. | 174/84 C |
| 4,998,936 | A * | 3/1991 | Mehdian | 606/250 |
| 5,133,716 | A * | 7/1992 | Plaza | 606/250 |
| 5,312,405 | A | 5/1994 | Korotko et al. | |
| 5,643,260 | A | 7/1997 | Doherty | |
| 5,885,284 | A | 3/1999 | Errico et al. | |
| 5,928,231 | A * | 7/1999 | Klein et al. | 606/60 |
| 6,136,003 | A * | 10/2000 | Hoeck et al. | 606/252 |
| 6,267,764 | B1 | 7/2001 | Elberg | |
| 6,872,208 | B1 * | 3/2005 | McBride et al. | 606/86 A |
| 6,880,224 | B2 * | 4/2005 | Colarusso et al. | 29/456 |
| 6,966,910 | B2 | 11/2005 | Ritland | |
| 7,641,673 | B2 * | 1/2010 | Le Couedic et al. | 606/259 |
| 2002/0138077 | A1 * | 9/2002 | Ferree | 606/61 |
| 2003/0171749 | A1 * | 9/2003 | Le Couedic et al. | 606/61 |
| 2004/0049189 | A1 | 3/2004 | Couedic et al. | |
| 2004/0111088 | A1 * | 6/2004 | Picetti et al. | 606/61 |
| 2005/0065514 | A1 * | 3/2005 | Studer | 606/61 |
| 2005/0131405 | A1 * | 6/2005 | Molz et al. | 606/61 |
| 2005/0143823 | A1 * | 6/2005 | Boyd et al. | 623/17.16 |
| 2005/0154388 | A1 * | 7/2005 | Roussouly et al. | 606/61 |
| 2005/0228378 | A1 | 10/2005 | Kalfas et al. | |
| 2005/0261685 | A1 * | 11/2005 | Fortin et al. | 606/61 |
| 2005/0277926 | A1 | 12/2005 | Farris | |
| 2005/0277932 | A1 | 12/2005 | Farris | |
| 2006/0009768 | A1 * | 1/2006 | Ritland | 606/61 |
| 2006/0064090 | A1 * | 3/2006 | Park | 606/61 |
| 2006/0079892 | A1 * | 4/2006 | Roychowdhury et al. | 606/61 |
| 2006/0142760 | A1 | 6/2006 | McDonnell | |
| 2006/0184171 | A1 * | 8/2006 | Biedermann et al. | 606/61 |
| 2006/0229608 | A1 * | 10/2006 | Foster et al. | 606/61 |
| 2006/0229611 | A1 * | 10/2006 | Avery et al. | 606/61 |
| 2006/0247627 | A1 * | 11/2006 | Farris | 606/61 |
| 2006/0264935 | A1 * | 11/2006 | White | 606/61 |
| 2007/0173825 | A1 * | 7/2007 | Sharifi-Mehr et al. | 606/61 |

* cited by examiner

*Primary Examiner* — Eduardo C Robert
*Assistant Examiner* — Jerry Cumberledge (57) ABSTRACT

A spinal stabilization system includes a first stabilization member and a second stabilization member engaged to one another in end-to-end fashion. A flexible coupling member allows the spinal stabilization members to be assembled and attached to the spinal column to dynamically support of the stabilized levels of the spinal column.

33 Claims, 9 Drawing Sheets

FLEXIBLE COUPLING MEMBERS FOR SPINAL STABILIZATION MEMBERS

BACKGROUND

The spine is subject to various pathologies that compromise its load bearing and support capabilities. Such pathologies of the spine include, for example, degenerative diseases, the effects of tumors and, of course, fractures and dislocations attributable to physical trauma. In the treatment of diseases, malformations or injuries affecting spinal motion segments (which include two or more adjacent vertebrae and the disc tissue or disc space therebetween), and especially those affecting disc tissue, it has long been known to remove some or all of a degenerated, ruptured or otherwise failing disc. It is also known that artificial discs, fusion implants, or other interbody devices can be placed into the disc space after disc material removal. External stabilization of spinal segments alone or in combination with interbody devices also provides advantages. Elongated rigid plates, rods and other external stabilization devices have been helpful in the stabilization and fixation of a spinal motion segment, in correcting abnormal curvatures and alignments of the spinal column, and for treatment of other conditions.

While external stabilization systems have been employed along the vertebrae, the geometric and dimensional features of these systems and patient anatomy constrain the surgeon during surgery and prevent optimal placement and attachment along the spinal column. For example, elongated, one-piece spinal rods can be difficult to maneuver into position along the spinal column, and also provide the surgeon with only limited options in sizing and selection of the rod system to be placed during surgery. Furthermore, there remains a need to provide spinal stabilization systems which correct one or more targeted spinal deformities while also preserving at least some spinal motion along one or more regions of the spine.

SUMMARY

Spinal stabilization systems are provided that include spinal stabilization members and at least one coupling member for securing the stabilization members along the spinal column in an end-to-end type arrangement. The coupling member includes a body with at least one hinge portion structured to flex or deform in response to movement of the spinal motion segment along which the stabilization members are attached. The stabilization members provide stabilization of the spinal column while at least limited motion of one or more of the supported levels of the spinal column is maintained with at least the coupling member.

In one form, a spinal stabilization system includes a first elongated stabilization member extending along a longitudinal axis between a first end and an opposite second end and a second elongated stabilization member extending along a longitudinal axis between a first end and an opposite second end. The system further includes a coupling member extending between a first end and an opposite a second end. The coupling member also includes at least a first receptacle for receiving the first end of the first stabilization member and a second receptacle for receiving the second end of the second stabilization member with the first stabilization member extending in a first direction away from the coupling member and the second stabilization member extending in a second direction away from the coupling member. The coupling member includes a deformable hinge portion between first and second body portions of the coupling member that permits movement of the first and second body portions of the coupling member relative to one another.

In yet another form, a coupling member for spinal stabilization members includes a body extending from a first end to a second end and includes opposite sides extending between the first and second ends. The body includes a first receptacle extending into the first end structured for engagement with an end of a first elongate spinal stabilization member. The body also includes a second receptacle extending therein from the second end of the body that is structured for engagement with an end of a second elongate spinal stabilization member. The first and second receptacles are situated such that the first and second spinal stabilization members extend in opposite directions from the respective end of the body. The body of the coupling member also includes at least one deformable hinge portion that is structured to provide movement of at least one portion of the body relative to another portion of the body in response to motion of the spinal column of a patient.

In a further form, a method for assembling a spinal stabilization system includes: providing a first elongate stabilization member with a first portion for attachment to the spinal column and an end portion; providing a second elongate stabilization member with a second portion for attachment to the spinal column and a second end portion; providing a coupling member including a hinge portion between first and second body portions of the coupling member; and connecting the first and second end portions of the first and second stabilization members with the coupling member to secure the stabilization members in a dynamic relationship relative to one another through deformation of the hinge portion of the coupling member.

Related features, aspects, embodiments, objects and advantages of the present invention will be apparent from the following description.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Figure 1:
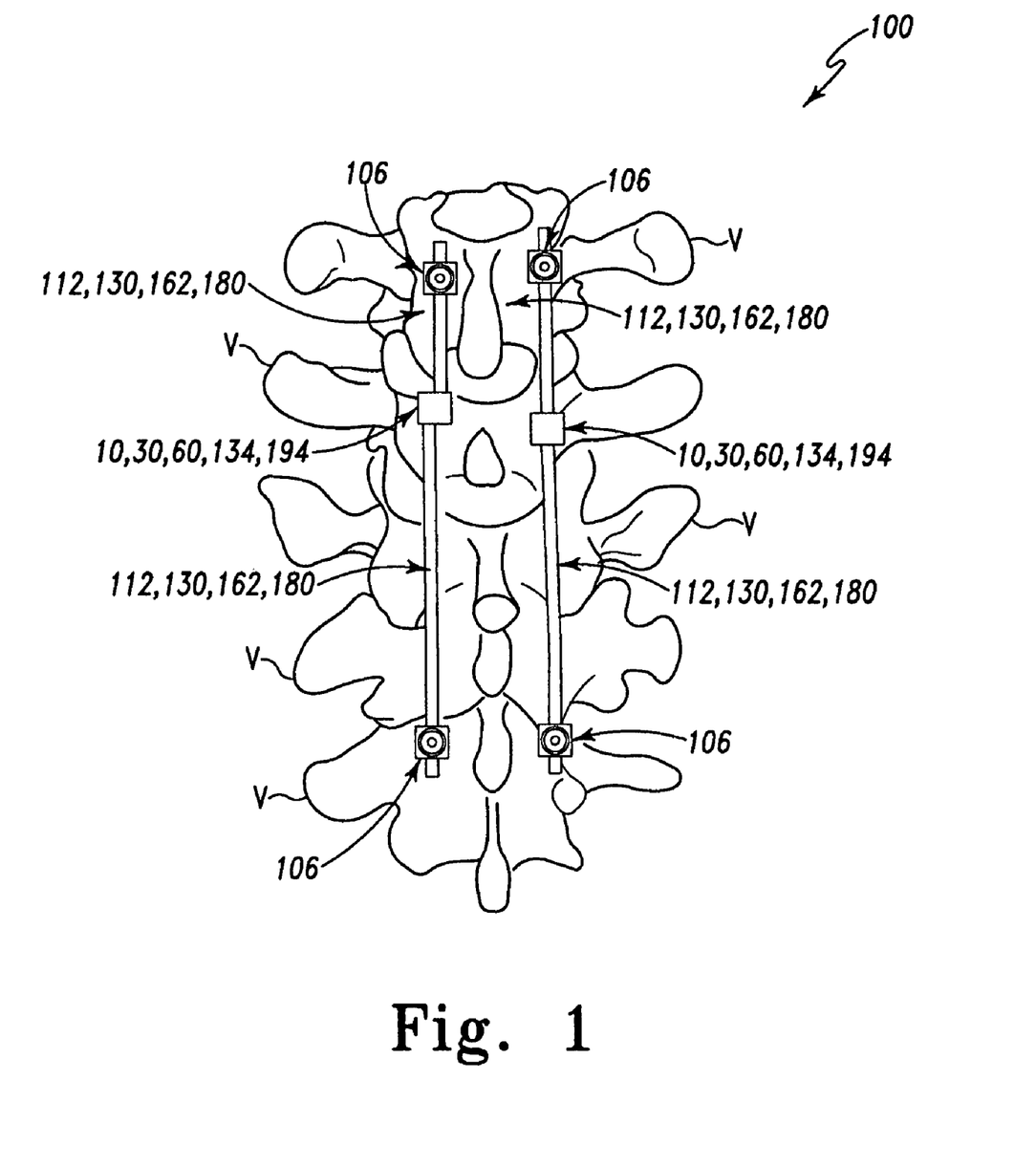
FIG. 1 is an elevation view of a posterior portion of the spinal column with stabilization systems shown diagrammatically in attachment with the spinal column.

FIG. 1 illustrates posterior spinal implant system 100 located along a spinal column of a patient. More specifically, implant system 100 can be affixed to vertebrae V of the spinal column segment from a posterior approach. Implant system 100 generally includes one or more coupling members 10, 30, 60, 134, 194 (shown diagrammatically and discussed further below) and elongated stabilization members 112, 130, 162, 180 (shown diagrammatically and discussed further below) that are structured to selectively interconnect with coupling members 10, 30, 60, 134, 194. Stabilization members 112, 130, 162, 180 may be a spinal rod, plate, bar, or other elongated element having a length to extend between at least two vertebrae. Stabilization members 112, 130, 162, 180 may be solid or hollow along some or all of its length and/or may be of homogenous or heterogeneous composition. In implant system 100, fastener assemblies 106 (shown diagrammatically) are affixed to various locations of the spinal column segment and secure stabilization members 112, 130, 162, 180 to selected vertebrae. Spinal implant system 100 may be used for, but is not limited to, treatment of degenerative spondylolisthesis, fracture, dislocation, scoliosis, kyphosis, spinal tumor, and/or a failed previous fusion. Applications in other approaches and implantation locations along the spinal column are also contemplated, including anterior, antero-lateral, and lateral approaches and locations.

Figure 2:
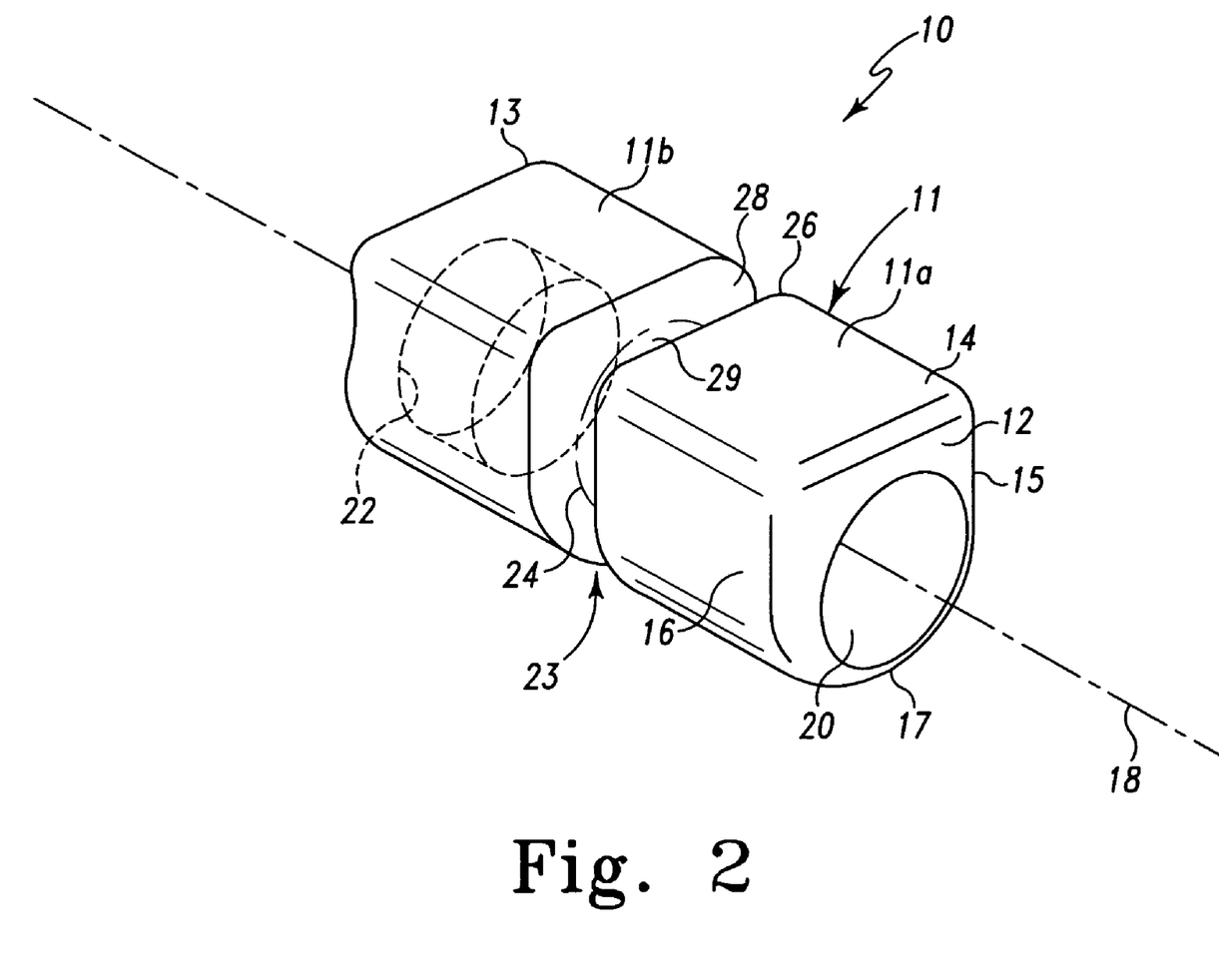
FIG. 2 is a perspective view of one embodiment coupling member for spinal stabilization members.

FIG. 2 illustrates in perspective view one embodiment of a coupling member 10 for securing elongate spinal stabilization members in end-to-end fashion along the spinal column. Coupling member 10 includes a body 11 extending between a first end 12 and an opposite second end 13. Body 11 generally has a rectangular block-type shape with a substantially rectangular outer cross sectional profile as defined by opposite side walls 14 and 17 and opposite side walls 15 and 16. Side wall 17 is illustrated with a partially arcuate shape. It should be appreciated that body 11 may include any number of different outer cross section profiles in other embodiments. For example, body 11 may include a triangular, rectangular, hexagonal, octagonal, oval, irregular or circular outer cross sectional profile in various other embodiments, just to name a few possibilities. Furthermore, it should be appreciated that each of side walls includes a dimension that is suited for implantation in the patient along the spinal column in a spinal surgical procedure.

Body 11 is elongated and generally extends along longitudinal axis 18 and includes a first receptacle 20 and a second receptacle 22, with each of receptacles 20, 22 extending in a direction substantially parallel to longitudinal axis 18 and into body portion 11 from respective ones of the first and second ends 12, 13. Receptacles 20, 22 are generally structured to engage with an end of a respective elongate spinal stabilization member such that the spinal stabilization members are interconnected by coupling member 10 in an end-to-end relationship. While receptacles 20, 22 are illustrated in substantial axial alignment with one another in FIG. 2, it should be appreciated that in other embodiments receptacles 20, 22 may be offset from one another and/or from longitudinal axis 18 while still providing an end-to-end coupling arrangement with the spinal stabilization members. Furthermore, it should be appreciated that receptacles 20, 22 may extend in any one or more directions in an oblique orientation relative to axis 18.

Coupling member 10 includes a deformable hinge portion 23 which extends between first and second body portions 11a, 11b of body 11. Hinge portion 23 forms a connecting stem 29 between the first and second body portions 11a, 11b, which house respective ones of the first and second receptacles 20 and 22. In the illustrated embodiment, hinge portion 23 is defined by a recess 24 extending into one or more of the side walls 14, 15, 16 and 17. Recess 24 forms a groove that is annular or partially annular around body 11 so that the cross-section of hinge portion 23 is smaller than the cross-section of the body portions 11a, 11b immediately adjacent hinge portion 23. In the illustrated embodiment, hinge portion 23 extends between a first wall section 26 and a second wall section 28 which opposingly face each other along recess 24, and stem 29 extends between and is integrally formed with wall sections 26, 28. As best shown in elevation view in FIG. 3, hinge portion 23 includes a width $W_1$ corresponding to the distance between wall sections 26 and 28. Furthermore, hinge portion 23 is formed at a depth $D_1$ from one or more of the side walls 14, 15, 16, 17. Depth $D_1$ includes a dimension corresponding to the distance between the bottom 24a of recess 24 and the exterior surface of body portions 11a and 11b.

Figure 3:
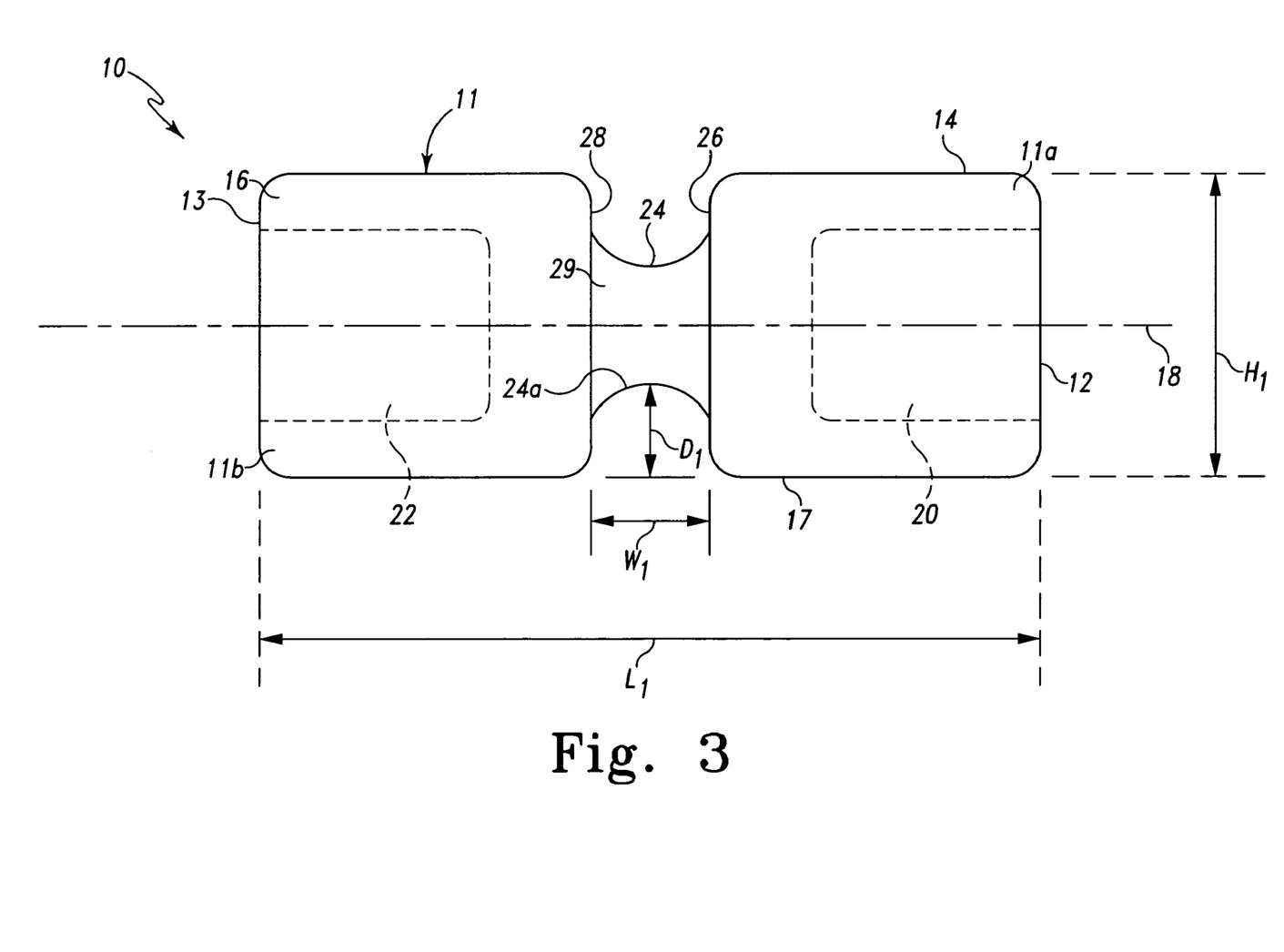
FIG. 3 is an elevation view of the coupling member in FIG. 2 with some features shown in phantom.

When situated at an implanted location along the spinal column of the patient, longitudinal axis 18 extends in a direction substantially parallel to the central axis of the spinal column of a patient. Furthermore, hinge portion 23 is flexible by deformation in a plurality of directions relative to longitudinal axis 18, as well as to the spinal column of the patient. Hinge portion 23 is configured to flex in any direction relative to longitudinal axis 18, or in one or more controlled directions so that movement is constrained in one or more predetermined planes. Coupling member 10 may be used in a spinal stabilization member system to preserve any number of ranges of motion of a patient, including but not limited to, any combination of flexion, extension, lateral bending, and lateral rotation.

Coupling member 10, as well as the other embodiment coupling members discussed herein, will provide varying degrees of flexibility to control patient motion in at least two ways. First, the coupling member will generally have limits on the total range of flexibility it provides by varying the material comprising the coupling member. More rigid material will provide less flexibility and lesser ranges of motion, while more flexible material will provide greater ranges of motion. Second, the flexibility of the coupling member can be varied by the geometry of the coupling member and its hinge portion. For example, the range of flexibility of the coupling member provides and its rigidity or stiffness are controlled by altering one or more of width $W_1$, depth $D_1$ and the material comprising the coupling member. In one form, the width $W_1$ and depth $D_1$ of recess 24 allow first and second portions 11a, 11b to move toward each other with hinge portion 23 acting like a shock absorber. In another form, hinge portion 23 bends to allow the angulation of one or both of body portions 11a, 11b to be varied relative to longitudinal axis 18 and relative to one another. The hinge portion 23 can be elastic to return towards its pre-deformed condition when the loading is removed from coupling member 10, or in-elastic so that the deformed condition is retained until further deformed by additional loading of the coupling member.

The amount of motion of the stabilization vertebral levels can be limited by the material properties of hinge portion 23 and/or by contact between body portions 11a, 11b. For example, compression or bending can be limited when body portions 11a, 11b contact one another. Increasing one or both of width $W_1$ and depth $D_1$ can increase the flexibility of coupling member 10 and the range of motion of the stabilized vertebral levels. Alternatively, decreasing one or both of width $W_1$ and depth $D_1$ around all or a portion of hinge portion 23 provides increased stiffness and reduces the range and amount of motion preserved by hinge portion 23.

The dimension of width $W_1$ may be altered in relation to the overall length $L_1$ of coupling member 10 in order to control the total amount of flexibility provided by coupling member 10. For example, in an embodiment where a greater amount of flexibility is desired, the dimension of width $W_1$ may be increased relative to length $L_1$, providing a greater distance between wall sections 26 and 28 such that coupling member 10 may be flexed over a greater range before wall sections 26 and 28 contact one another and prevent further flexion. It is also contemplated that the dimension of width $W_1$ may be decreased in relation to length $L_1$ for correction of one or more spinal deformities in which a smaller range of motion is desired.

Furthermore, it is contemplated that the rigidity of coupling member 10 as well as the amount of force required to flex coupling member 10 in one or more directions may be altered by changing, amongst other variables, the dimension of depth $D_1$ of recess 24 in relation to the dimension of overall height $H_1$ of coupling member 10. It should be understood that, generally speaking, as the dimension of depth $D_1$ increases relative to the dimension of height $H_1$, the rigidity of coupling member 10 and the amount of force necessary to flex coupling member 10 in one or more directions will both decrease. Moreover, as the dimension of depth $D_1$ decreases relative to the dimension of height $H_1$, the rigidity of coupling member 10 and the amount of force necessary to flex coupling member 10 in one or more directions both increase. Therefore, it is contemplated the dimension of depth $D_1$ of recess 24 may be altered in various embodiments to provide coupling members that correspond to various rigidity requirements.

It is contemplated that the dimension of one or both of depth $D_1$ and width $W_1$ may be changed to alter the rigidity of coupling member 10 in relation to one or more regions of the spinal column and/or in accordance with a desired therapeutic effect. It should be appreciated that as the dimension of depth $D_1$ and width $W_1$ of recess 24 increases, the dimension corresponding to the perimetrical configuration of recess 24 will decrease and become smaller in relation to the dimension of the perimetrical configuration of the remainder of body 11 adjacent recess 24. While it is contemplated that the dimension of depth $D_1$ and width $W_1$ may vary in other embodiments, it should be appreciated that the dimension of depth $D_1$ and width $W_1$ may not be increased to an amount which might jeopardize the integrity of the implant. For example, the cross-section of connecting stem 29 must be great enough to prevent stem 29 from breaking or fracturing upon repeated movement and flexing of coupling member 10. It should be appreciated that the dimension of the perimetrical configuration of connecting stem 29 required to prevent such occurrences may vary in relation to the amount of flexibility provided by coupling member 10 and the material of which connecting stem 29 is composed.

It should be appreciated that both the dimension of width $W_1$ and the dimension of depth $D_1$ of recess 24 may be altered alone or in combination with one another in various embodiments. For example, in one form, the dimension of width $W_1$ may be relatively small creating a small range of flexibility while the dimension of depth $D_1$ is relatively large such that the coupling member 10 is readily flexed between various configurations. In another form, the dimension of width $W_1$ may be relatively large while the dimension of depth $D_1$ is relatively small, such that the coupling member 10 includes a broad range of flexibility but requires a stronger force to move between various configurations. Still, other variations are contemplated beyond those set forth herein.

Figure 4:
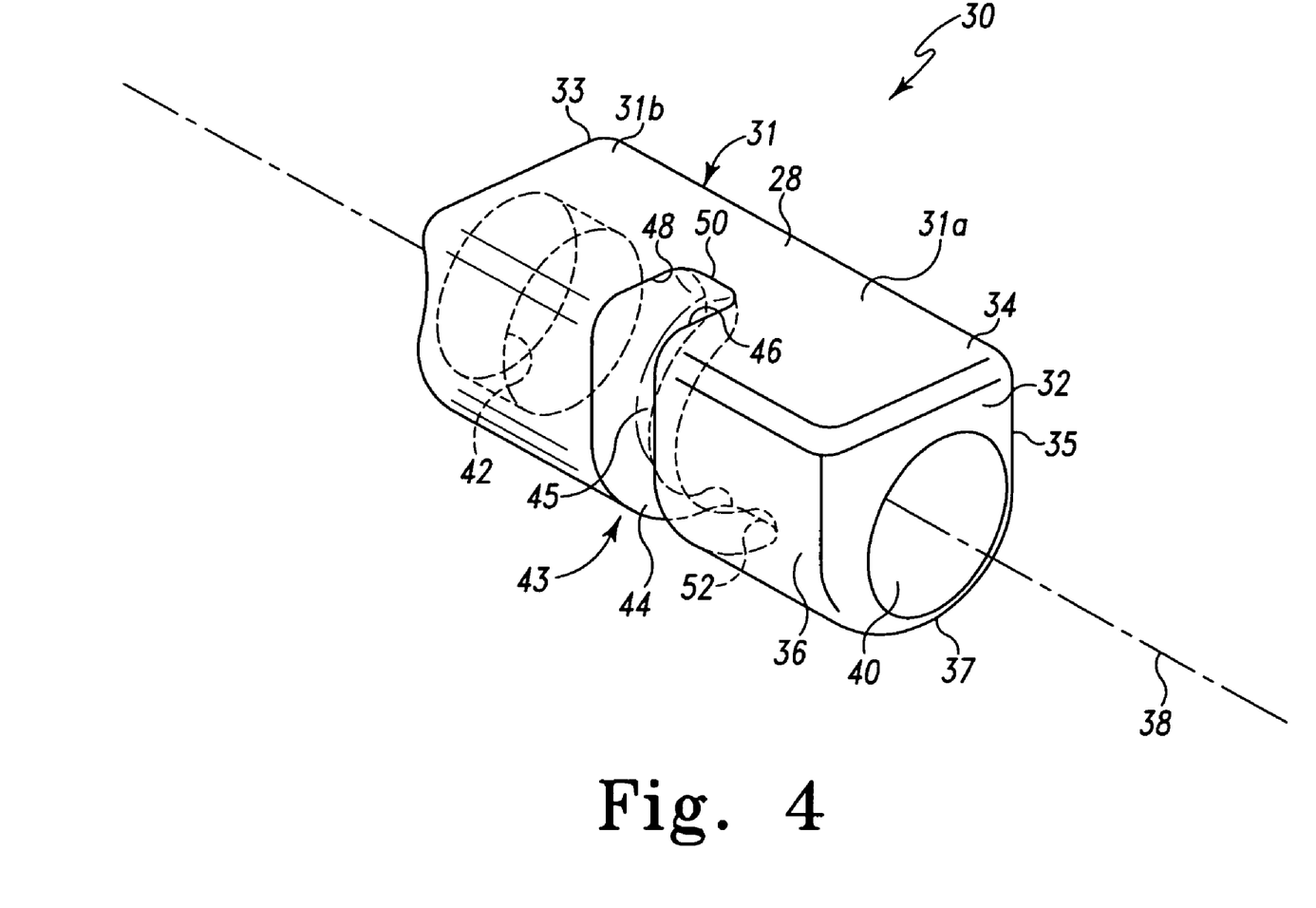
FIG. 4 is a perspective view of another embodiment coupling member with some features shown in phantom.

Referring now to FIG. 4 there is shown in perspective view another embodiment coupling member 30. Coupling member 30 includes a body 31 extending along longitudinal axis 38 between a first end 32 and a second end 33. Body 31 of coupling member 30 generally includes a substantially rectangular outer cross section including opposite side walls 34, 37 and opposite side walls 35, 36 extending between first and second ends 32, 33. Side wall 37 is shown with an arcuate shape. As discussed above in relation to coupling member 10, it should be appreciated that body 31 may be of any suitable shape and cross-section profile. For example, body 31 may include a rectangular, hexagonal, octagonal, oval, irregular or circular outer cross section in various other embodiments.

Body 31 includes a first receptacle 40 extending therein from first end 32, and a second receptacle 42 extending therein from second end 33. Each of receptacles 40, 42 are structured to receive and engage a respective end of an elongate spinal stabilization member such that the respective spinal stabilization members are connected in end-to-end fashion. It should be appreciated that each of receptacles 40, 42 may vary in accordance with the variations set forth above in regard to receptacles 20, 22. Coupling member 30 further includes a hinge portion 43 forming a connection stem 45 disposed between and integrally formed with first and second body portions 31a, 31b of body 31. First and second body portions 31a, 31b house respective ones of the first and second receptacles 40, 42.

In the embodiment of FIG. 4, hinge portion 43 is defined by a recess 44. Recess 44 is in the form of a concave groove that extends generally around about one half of body 31 from a first terminal end 50 disposed substantially in the middle of side wall 34 to a second terminal end 52 disposed substantially in the middle of side wall 37. A dimension corresponding to the perimetrical configuration of hinge portion 43 is generally smaller than the dimension corresponding to the perimetrical configuration of the remainder of body 31. Recess 44 is defined between a first wall section 46 and a second wall section 48 which may move toward one another upon the application of a flexing force on coupling member 30. It should be appreciated that recess 44 includes a width dimension and a depth dimension which may be altered to achieve various desired flexibility and rigidity properties of coupling member 30, as discussed above in regard to recess 24 of coupling member 10.

It should be appreciated that the structure and placement of recess 44 on coupling member 30 provides different ranges of motion for coupling member 30. Stem 45 is offset in an eccentric arrangement relative to longitudinal axis 38 with body portions 31a, 31b concentrically disposed about longitudinal axis 38. In this arrangement, motion of the stabilization members toward and away from one other is less along stem 45 than along recess 44. Since stem 45 includes a thickness that extends to the side walls 34, 37, bending in the direction between side walls 34, 37 will be less than the bending in the direction between side walls 35, 36. Coupling member 30 may be used to permit spinal motion in one direction while limiting it or preventing it in a direction along which the thickness of stem 45 between side walls 34, 37 is oriented. For example, coupling member 30 may be placed in a spinal stabilization system such that recess 44 faces in a posterior or anterior direction to allow flexion and extension, while side walls 34, 37 are oriented medially and laterally so that stem 45 is situated to limit or prevent motion as a result of lateral bending. In one or more additional forms, recess 44 may face in any desired direction relative to the spinal column of a patient when implanted.

Figure 5:
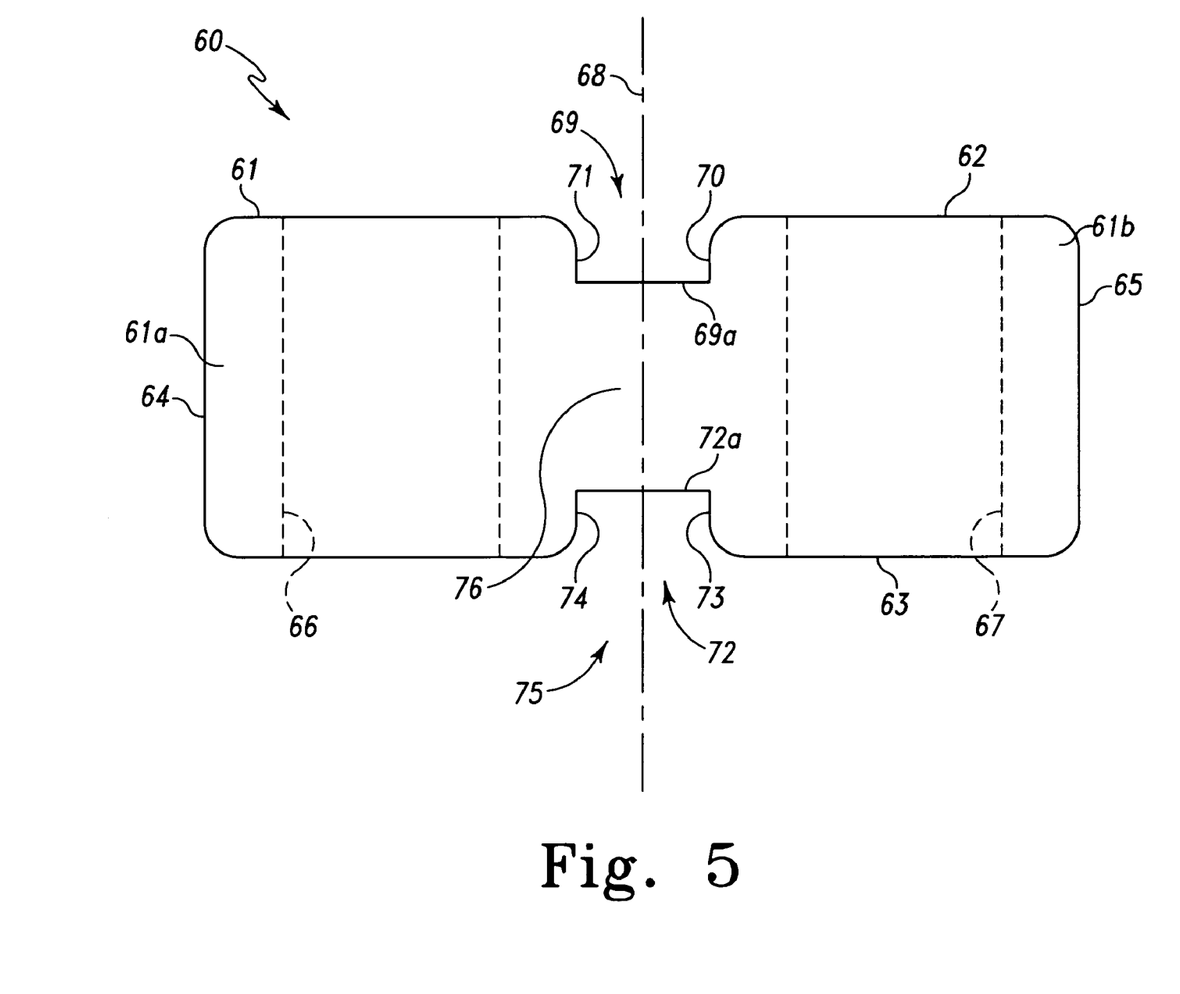
FIG. 5 is an elevation view of another coupling member with some features shown in phantom.

In FIG. 5 there is shown in elevation view another embodiment coupling member 60 including a body 61 extending between a first end 62 and an opposite second end 63 along central axis 68. In this form, coupling member 60 includes a first receptacle 66 and second receptacle 67 which each extend in a direction substantially parallel to central axis 68 and opening at each of first and second ends 62, 63. Each of receptacles 66, 67 is structured to engage with an end of a respective elongate spinal stabilization member such that the spinal stabilization members are interconnected in an end-to-end fashion by coupling member 60 while in an offset relation to central axis 68. As illustrated, receptacles 66, 67 extend through both of the ends 62, 63 such that one or more of the respective spinal stabilization members may extend entirely through coupling member 60, facilitating interconnection of respective spinal stabilization members having end portions which extend beyond each other. Other embodiments contemplate that one or both of receptacles 66, 67 include a blind end in body 61.

Coupling member 60 also includes a hinge portion 75 including a pair of recesses 69, 72 which extend between first and second body portions 61a, 61b and form a coupling member stem 76. As illustrated, recesses 69, 72 are each generally rectangular shaped and include respective terminal walls 69a and 72a and respective wall sections 70, 71 and 73, 74. It should be appreciated that in other embodiments recesses 69, 72 may be shaped differently, like for example, they may be concavely curved, triangular, or irregular just to name a few possibilities. Body portion 61a extends from stem 76 to a side wall 64, and body portion 61b extends from stem 76 to side wall 65.

As discussed above, it should be appreciated that the placement and structure of recesses 69, 72 determine the overall flexibility and rigidity of coupling member 60. For example, it should be understood that recesses 69, 72 generally facilitate flexion of one or both body portions 61a, 61b about central axis 68. It should be appreciated that in other embodiments not shown, recesses 69, 72 may form a single recess extending completely or partially around body portion 61 of coupling member 60 to provide flexion of coupling member 60 in various alternative directions. Furthermore, it should be appreciated that the width and depth of recesses 69, 72 may be modified to alter one or both of the rigidity of coupling member 60 and the range of flexibility it provides.

It should be appreciated that each of coupling members 10, 30, 60 may include any one or more features described in regard to any other of coupling members 10, 30, 60 in addition to or in lieu of the features described in association therewith. It is further contemplated that any of coupling members 10, 30, 60 may include one or more hinge portions in addition to or in lieu of any of the hinge portions described in association therewith. In one form, the additional one or more hinge portions may provide flexibility of the coupling member in a direction the same as or in one or more directions in addition to the flexibility provided by the described hinge portions. Furthermore, in an embodiment including more than one hinge portion, it is contemplated that each hinge portion may individually vary in one or more of its rigidity, direction(s) of flexibility provided, and the amount of flexibility provided.

It should be appreciated that each of the coupling members 10, 30, 60 contemplated herein may be composed of a single material or may be composed of a plurality of materials. For example, in one form the coupling member may be formed of one or more of medical grade stainless steel, titanium, chrome-cobalt, nitinol or other shape memory alloys, and one or more polymers. It is further contemplated that one or more portions of the coupling member may be formed from a first material while another portion is formed from a different second material. For example, in one specific embodiment, the flexible section of the coupling member is formed from a polymer while the rest of the coupling member is formed of metallic material. The composite structure provides more flexibility to a target region or focused location of the coupling member, such as the hinge portion, while providing the portions secured to the stabilization members with a more rigid structure to facilitate engagement of the stabilization member thereto. In another form, one or more of the coupling members and the stabilization members may comprise one or more materials the same or different from each other.

It should further be appreciated that the selection of material comprising the coupling member may vary in relation to the selected flexibility and rigidity characteristics of the hinge portion, as discussed above. A material having certain elasticity properties may be selected in one form to control the return of the coupling member to its unflexed position when a flexion force is no longer applied to the coupling member. In another form, the material may be stretchable or compressible to facilitate alterations to length L of the coupling member upon the application of various axial forces to the coupling member. It is further contemplated that the structure and placement of the hinge portion(s) along with the selection of the material(s) comprising the coupling member may be modified in order to obtain a coupling member having desired flexible properties. In one form, the structure and placement of the hinge portion(s) along with the selection of material comprising the coupling member may be such that the coupling member mimics the strength and flexibility of tendons, muscles, or ligaments along one or more sections of the spinal column. It should be appreciated that the coupling members contemplated herein may each be individually modified to address various applications requiring various flexible and rigid configurations.

Referring now generally to FIGS. 6-9 there is illustrated flexible spinal stabilization systems in which one or more coupling members 10, 30, 60 may be employed. In the embodiments illustrated herein, although only one coupling member is shown, one or more of the illustrated first and second stabilization members can be adapted for engagement with another coupling member at each end thereof so that three or more stabilization members may comprise the stabilization system. The stabilization members include stabilization member portions extending from the coupling member or members which are secured to vertebrae of the spinal column system with any one or combination of hooks, screws, bolts, multi-axial screws, staples, cables or wires, sutures, clamps, and/or other attachment devices and systems, with or without interbody fusion devices or implants between vertebrae.

The coupling members contemplated herein allow stabilization members of differing characteristics and stabilization members having the same characteristics to be flexibly secured to one another in end-to-end fashion to provide a stabilization system that is adapted for the anatomy, surgical condition, or surgical procedure. In one embodiment, the characteristic includes a cross-sectional dimension of the stabilization member portions so that stabilization members of differing sizes can be secured along the spinal column and to one another in end-to-end fashion. Other embodiments contemplate selection criteria for selection and assembly of the stabilization member portion to include any one or combination of characteristics, including length, contouring, flexibility, surface features, shape, section modulus, elasticity, materials and material properties, and coatings, for example.

Figure 6:
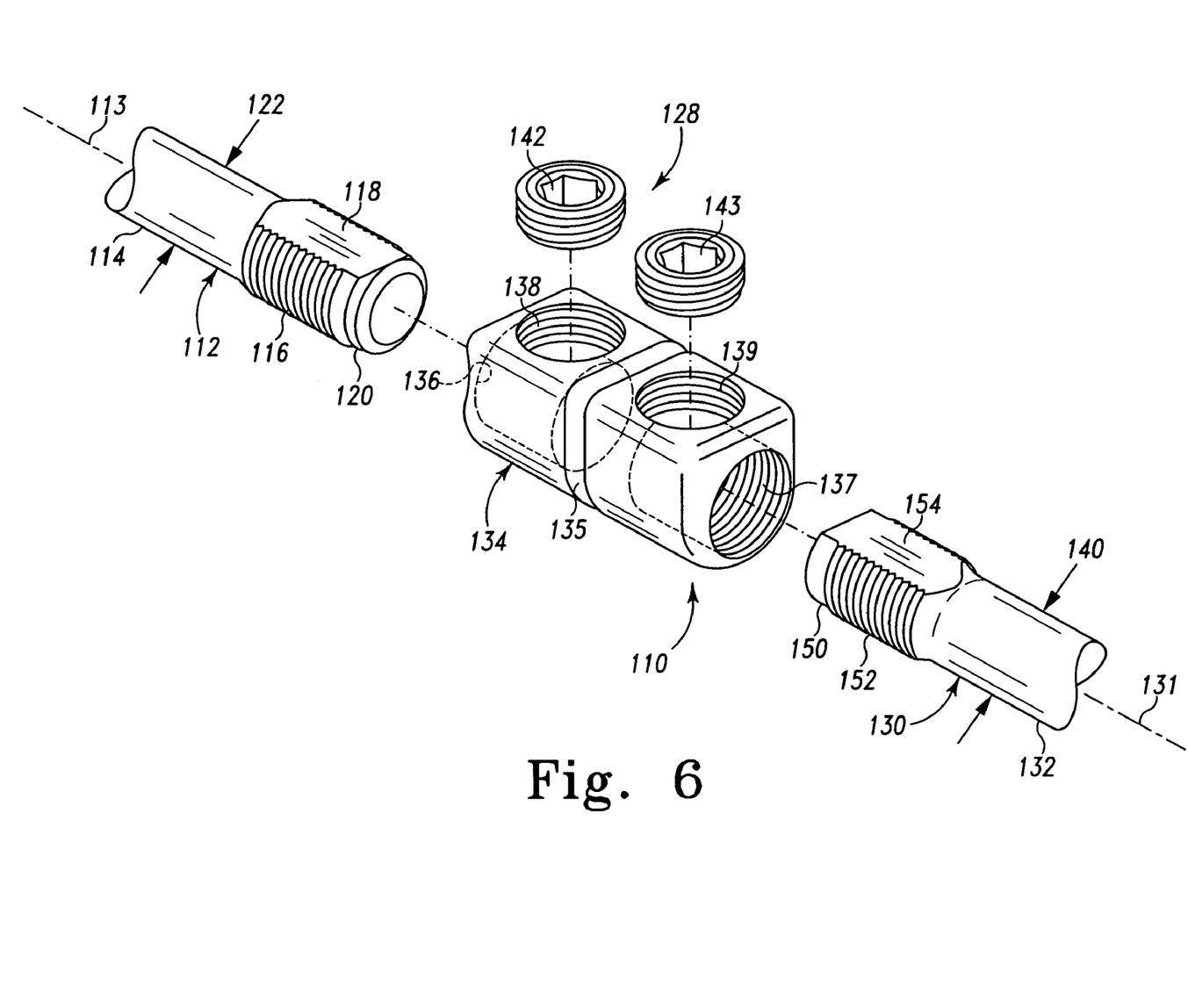
FIG. 6 is an exploded perspective view of a portion of a spinal stabilization system.
Figure 7:
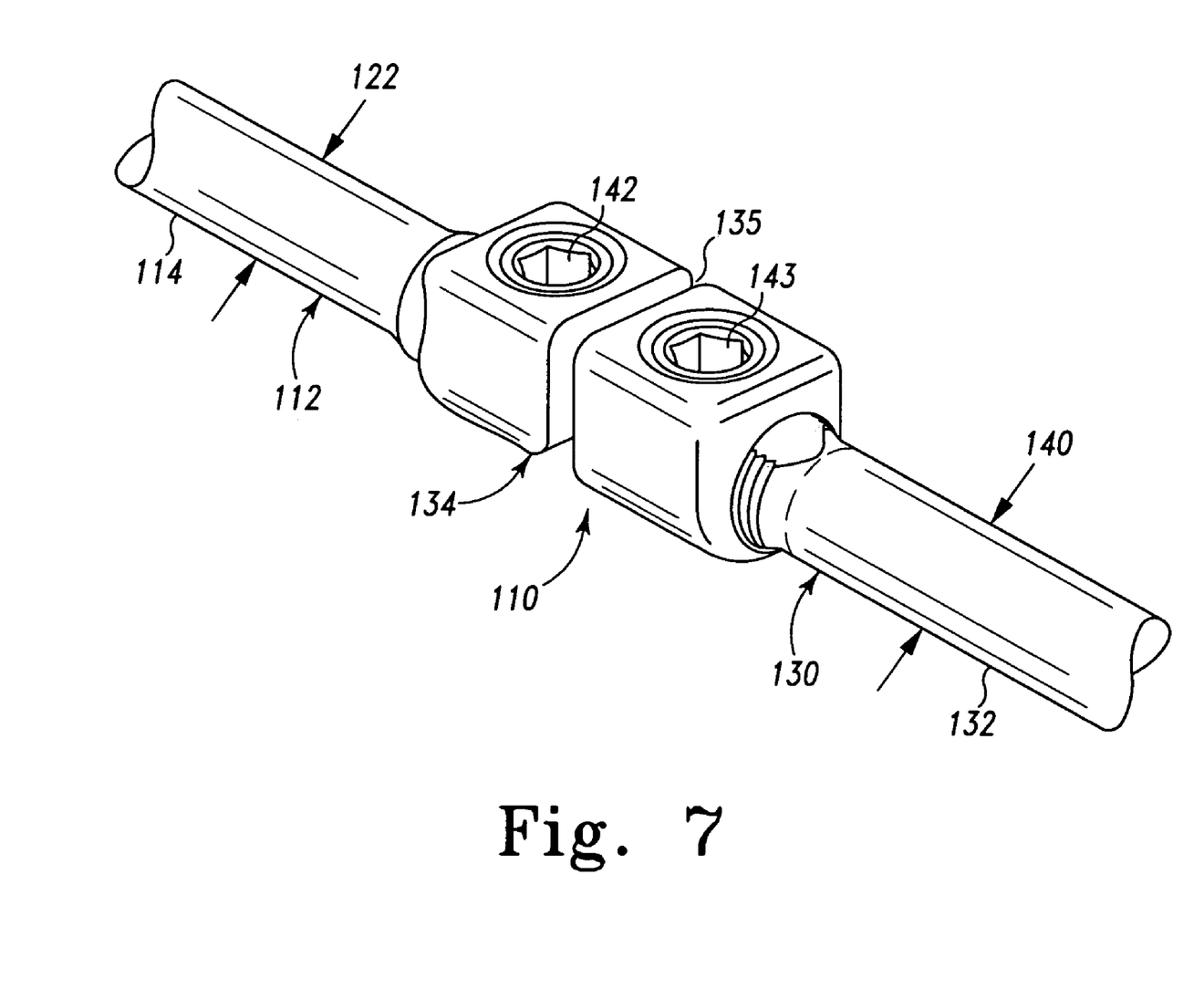
FIG. 7 is an assembled perspective view of the spinal stabilization system of FIG. 6.

In FIGS. 6-7 there is shown a spinal stabilization system 110 including a first elongate stabilization member 112 and a second elongate stabilization member 130. First stabilization member 112 and second stabilization member 130 are releasably coupled to one another in end-to-end fashion with coupling mechanism 128. Coupling mechanism 128 includes a coupling member 134 releasably engageable to each of the first and second stabilization members 112, 130. The coupling member 134 is configured to secure stabilization members 112, 130 in end-to-end fashion while minimizing the footprint or intrusiveness of the coupling mechanism into the tissue surrounding the stabilization system and maximizing the length of the portion of each stabilization member available for positioning and/or attachment along the spinal column. Furthermore, as illustrated, coupling member 134 includes a hinge portion 135 connecting first and second body portions of coupling member 134. Hinge portion 135 is similar to hinge portion 23 as described in relation to coupling member 10. Hinge portion 135 facilitates flexion of coupling member 134 in any one or more directions relative to axes 113, 131 of stabilization members 112, 130 creating a dynamic stabilization system 110 which allows at least limited motion of one or more regions of the spinal column along which the system is engaged.

First stabilization member 112 includes a first member portion 114 and end portion 116 at a first end of first member portion 114. First member portion 114 extends from end 116 to an opposite second end (not shown.) Second stabilization member 130 includes end portion 152 at a first end thereof. Second member portion 132 extends from end portion 152 to an opposite second end (not shown.) One or both of the second ends of first and second member portions 114, 132 may include an end portion that is same as the end portion shown or that simply provides a terminal end shaped like the corresponding member portion 114, 132 as shown.

First member portion 114 can be provided with a characteristic that differs from a characteristic of second member portion 132. The coupling member 134 allows stabilization members of differing characteristics to be secured to one another in end-to-end fashion to provide a stabilization system that is adapted for the anatomy, surgical condition, or surgical procedure. In one embodiment, the characteristic includes a cross-sectional dimension of the first and second member portions 114, 132. Other embodiments contemplate selection criteria for selection and assembly of the first and second member portions to include any one or combination of characteristics, including length, contouring, flexibility, surface features, shape, section modulus, elasticity, materials and material properties, and coatings, for example. In still other embodiments, first and second member portions 114, 143 are provided with the same or substantially identical characteristics.

As shown in FIGS. 6-7, first member portion 114 extends along longitudinal axis 113 and includes a first cross-sectional dimension 122 between opposite sides thereof transverse to longitudinal axis 113. Similarly, second member portion 132 extends along longitudinal axis 131 and includes a second cross-sectional dimension 140 between opposite sides thereof transverse to longitudinal axis 131. In the illustrated embodiment, cross-sectional dimension 122 corresponds to a diameter of a cylindrically shaped member portion 114 that is smaller than a diameter corresponding to cross-sectional dimension 140 of a cylindrically shaped member portion 132. In other embodiments, the diameters are the same. In one specific application, the diameter of first member portion 114 is sized to extend along a first portion of the spine, such as the cervical region, and the diameter of second member portion 132 is sized to extend along a second portion of the spine, such as the thoracic region. Other systems contemplate multiple member portions coupled to one another in end-to-end fashion with characteristics adapted for positioning along any one or combination of the sacral, lumbar, thoracic and cervical regions of the spinal column.

In the illustrated embodiment, end portion 116 includes a threaded outer surface extending from member portion 114 to an end member 120 lacking threads. End portion 116 further includes a contact portion 118 along at least one side thereof. Contact portion 118 can be formed by a cutout providing a flat surface extending along end portion 116. Contact portion 118 can also include a concave surface, a convex surface, a receptacle, or other suitable configuration for contacting an engaging member. The thread pattern of end portion 116 can extend completely therearound between the opposite sides of contact portion 118. Other embodiments contemplate that multiple contact portions are provided along end portion 116 to provide multiple engagement locations for engaging member 142, as discussed further below, or that the end portion is threaded completely therearound, or that the end portion lacks any threads.

Stabilization member 130 similarly includes end portion 152 with a threaded outer surface extending from member portion 132 to an end member 150 lacking threads. End portion 152 further includes a contact portion 154 along at least one side thereof. Contact portion 154 can be formed by a cutout providing a flat surface extending along end portion 152. Contact portion 154 can also include a concave surface, a convex surface, a receptacle, or other suitable configuration for contacting an engaging member. The thread pattern of end portion 152 can extend completely therearound between the opposite sides of contact portion 154. Other embodiments contemplate that multiple contact portions are provided along end portion 152 to provide multiple engagement locations for engaging member 143, as discussed further below.

Coupling member 134 can be enlarged relative to first and member portions 114, 132 to provide a first axial receptacle 136 and a second axial receptacle 137 that threadingly receive the respective end portions 116, 152. First receptacle 136 and second receptacle 137 extend from a point adjacent hinge portion 135 and open at the ends of coupling member 134 along the same axis. Coupling member 134 further includes a first trans-axial bore 138 and an adjacent second trans-axial bore 139 extending therein transversely to receptacles 136, 137 and in communication with receptacles 136, 137. Bores 138, 139 can be internally threaded for receipt of respective ones of the engagement members 142, 143. Bores 138, 139 can be orthogonal to receptacles 136, 137, although other orientations are also contemplated.

Stabilization members 112, 130 are assembled in end-to-end fashion and aligned along longitudinal axes 113, 131 with end portion 116 received in receptacle 136 and end portion 152 received in receptacle 137. End portions 116, 152 are axially constrained by threaded engagement with coupling member 134. End members 120, 150 facilitate positioning and alignment of end portions 116, 152 in receptacles 136, 137, preventing or reducing the possibility of cross-threading end portions 116, 152 with coupling member 134. The axial load between stabilization members 112, 130 is carried by the engagement between end portions 116, 152 and coupling member 134. Accordingly, torsional loading of the components of stabilization system 110 is minimized since the stabilization members 112, 130 are connected to one another in end-to-end fashion with axes 113, 131 aligned via coupling member 134.

Engaging members 142, 143 are positionable in first trans-axial bore 138 and second trans-axial bore 139 and engageable to respective ones of the end portions 116, 152 to prevent stabilization members 112, 130 from disengaging from coupling member 134. In one embodiment, contact portion 118 of coupling member 116 is oriented toward first trans-axial bore 138, and engaging member 142 is an externally threaded set screw engageable in first trans-axial bore 138. Engaging member 142 is driven into first trans-axial bore 138 so that it is in contact with contact portion 118, preventing end portion 116 from rotating in coupling member 134 and resisting torsional loading from stabilization member 112. Similarly, contact portion 154 of end portion 152 is oriented toward second bore 139, and engaging member 143 is an externally threaded set screw engageable in second trans-axial bore 139. Engaging member 143 is driven into bore 139 so that it is in contact with contact portion 154, preventing end portion 152 from rotating in coupling member 134 and resisting torsional loading of stabilization member 130. It should be appreciated that any torsional loading on either of stabilization members 112, 130 and its loading on coupling member 134 is reduced through flexion at hinge portion 135 of coupling member 134.

Figure 8:
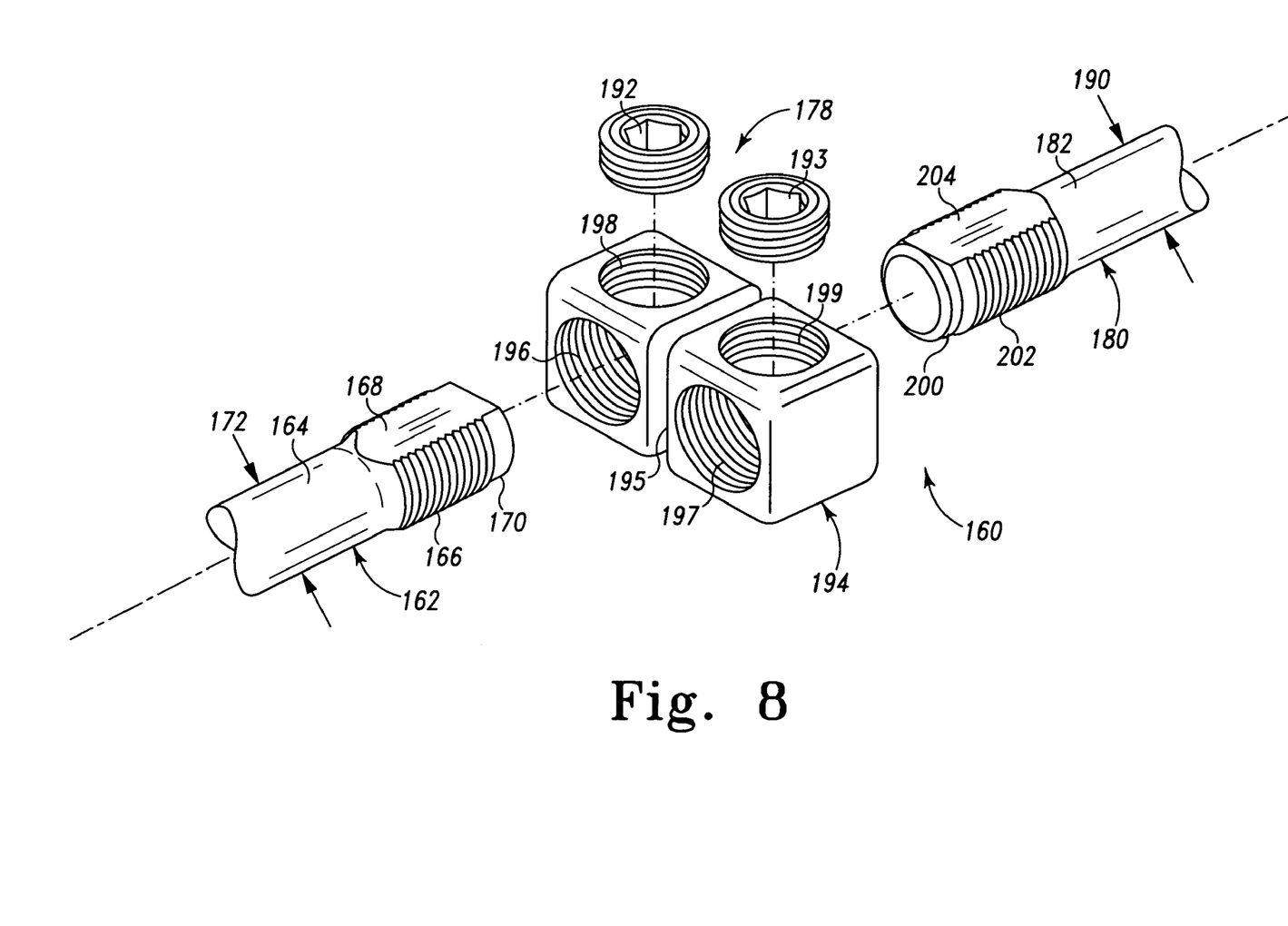
FIG. 8 is an exploded perspective view of a portion of another embodiment spinal stabilization system.
Figure 9:
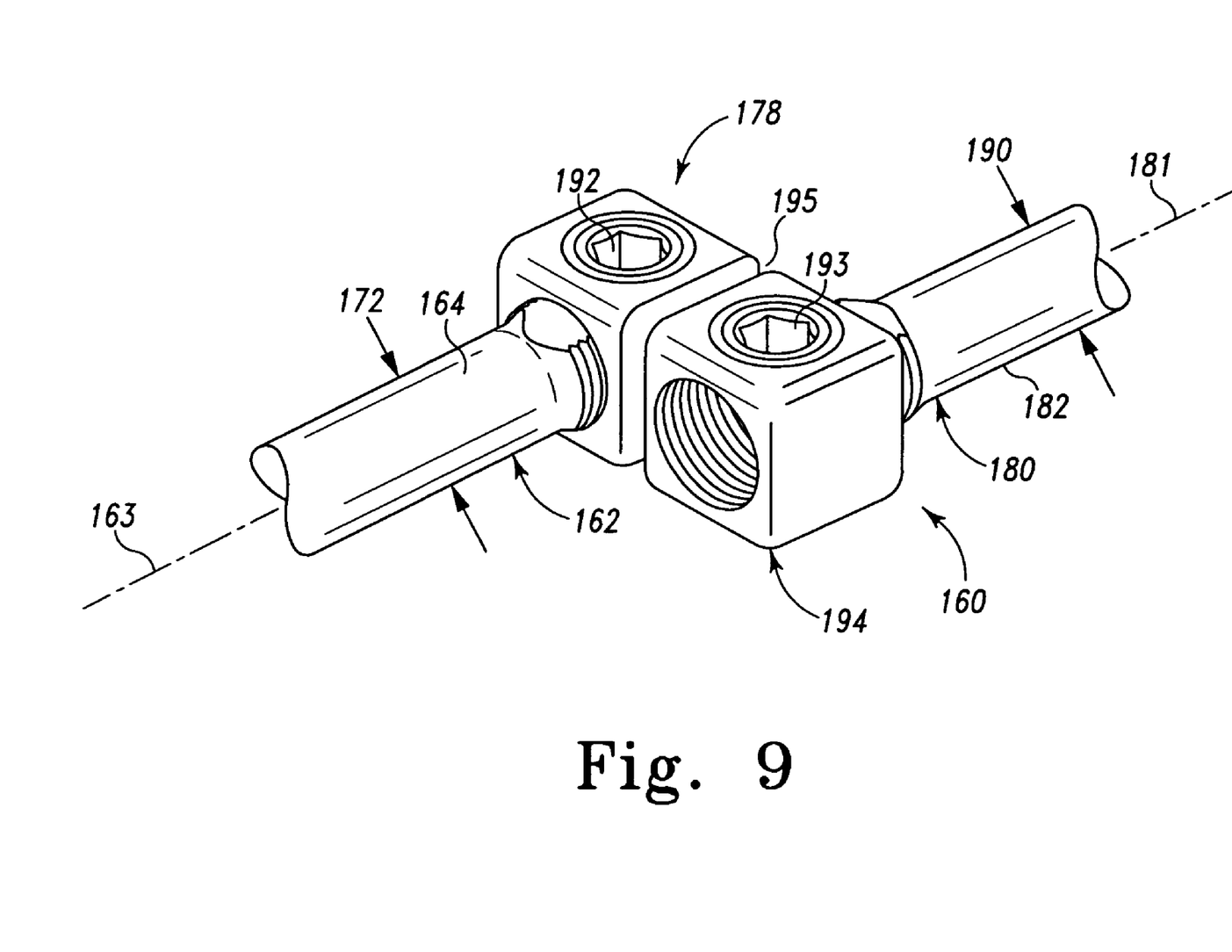
FIG. 9 is an assembled perspective view of the spinal stabilization system of FIG. 8.

Referring to FIGS. 8 and 9, there is shown another embodiment spinal stabilization system 160 including a first elongate stabilization member 162 and a second elongate stabilization member 180. First stabilization member 162 and second stabilization member 180 are releasably coupled to one another in end-to-end fashion with a coupling mechanism 178. Coupling mechanism 178 includes a coupling member 194 releasably engageable to each of the first and second stabilization members 162, 180. The coupling mechanism 178 is configured to secure stabilization members 162, 180 to one another in end-to-end fashion with their longitudinal axes 163, 181 laterally offset from one another. This allows the relative positioning of stabilization members 162, 180 to be offset as may be desirable to accommodate the spinal anatomy while minimizing the footprint or intrusiveness of the coupling mechanism into the tissue surrounding the stabilization system, and maximizing the length of the portions of each stabilization member available for positioning and/or attachment along the spinal column.

Coupling member 194 includes a hinge portion 195 between first and second body portions of coupling member 194. Hinge portion 195 is similar to hinge portion 75 as described in relation to coupling member 60. Hinge portion 195 facilitates flexion of coupling member 194, creating a dynamic stabilization system 160 which allows patient mobility across one or more regions of the spinal column. It should be appreciated that hinge portion 195 may be modified as described herein to alter the rigidity or range of flexibility of coupling member 194.

Like stabilization members 112, 130 discussed above, first stabilization member 162 includes a first member portion 164 and an end portion 166 at a first end of first member portion 164. First member portion 164 extends from end portion 166 to an opposite second end (not shown.) Second stabilization member 180 includes end portion 202 at a first end thereof. Second member portion 182 extends from end portion 202 to an opposite second end (not shown.) First and second member portions 164, 182 can be provided with substantially identical load supporting characteristics or with characteristics that differ from one another.

As shown in FIGS. 8-9 first member portion 164 extends along longitudinal axis 163 and includes a first cross-sectional dimension 172 between opposite sides thereof transverse to longitudinal axis 163. Similarly, second member portion 182 extends along longitudinal axis 181 and includes a second cross-sectional dimension 190 between opposite sides thereof transverse to longitudinal axis 181. In the illustrated embodiment, cross-sectional dimension 172 corresponds to a diameter of a cylindrical member portion 164 that is smaller than a diameter corresponding to cross-sectional dimension 190 of a cylindrical member portion 182. In still other embodiments, the diameters of member portions 164, 182 are the same.

Coupling member 166 includes a threaded outer surface extending from member portion 164 to an end portion 170 lacking threads. Coupling member 166 further includes a contact portion 168 along at least one side thereof. Contact portion 168 can be formed by a cutout providing a flat surface extending along end portion 166. Contact portion 168 can also include a concave surface, a convex surface, a receptacle, or other suitable configuration for contacting an engaging member. The thread pattern of end portion 166 can extend completely therearound between the opposite sides of contact portion 168. Other embodiments contemplate that multiple contact portions are provided along end portion 166 to provide multiple engagement locations for engaging member 192, as discussed further below. In still other embodiments, no contact portion is provided, and end portion 166 is completely threaded therearound, or completely lacks threads.

Stabilization member 180 similarly includes an end portion 202 including a threaded outer surface extending from first member portion 182 to an end member 200 lacking threads. End portion 202 further includes a contact portion 204 along at least one side thereof. Contact portion 204 can be formed by a cutout providing a flat surface extending along end portion 202. Contact portion 204 can also include a concave surface, a convex surface, a receptacle, or other suitable configuration for contacting an engaging member. The thread pattern of end portion 202 can extend completely therearound between the opposite sides of contact portion 204. Other embodiments contemplate that multiple contact portions are provided along end portion 202 to provide multiple engagement locations for engaging member 193, as discussed further below. In still other embodiments, no contact portion is provided, and end portion 202 is completely threaded therearound, or completely lacks threads.

Coupling member 194 can be enlarged relative to first and second member portions 164, 182 to provide an axial first receptacle 196 that threadingly receives end portion 166, and an axial second receptacle 197 offset laterally from and extending parallel to first receptacle 196 to threadingly receive end portion 202. In the illustrated embodiment, coupling member 194 is a rectangular block, although other shapes are also contemplated, such as cubic, cylindrical and non-uniform shapes. First receptacle 196 extends along and opens on longitudinal axis 163 when aligned with stabilization member 162, and second receptacle 197 extends along and opens on longitudinal axis 181 when aligned with stabilization member 180. Coupling member 194 further includes a first trans-axial bore 198 and an adjacent second trans-axial bore 199 extending therein transversely to respective ones of the longitudinal axes 163, 181 and in communication with respective ones of the receptacles 196, 197. Bores 198, 199 can be internally threaded for receipt of respective ones of the engagement members 192, 193. Bores 198, 199 can be orthogonal to the respective receptacles 196, 197, although other orientations are also contemplated.

Stabilization members 162, 180 can be assembled in end-to-end fashion with end portion 166 received in first receptacle 196 and end portion 202 received in second receptacle 197. End portions 166, 202 are axially constrained by threaded engagement with coupling member 194. End members 170, 200 facilitate positioning and alignment of end portions 166, 202 in receptacles 196, 197, preventing or reducing the possibility of cross-threading end portions 166, 202 with coupling member 194. The axial load between stabilization members 162, 180 is carried by the engagement between coupling members 166, 202 and coupling member 194.

The axial restraint provided by the threaded engagement of stabilization members 162, 180 to coupling member 194 allows the length of coupling member 194 along axes 163, 181 to be minimized, thus minimizing its intrusion into the adjacent anatomy and maximizing the stabilization member length available for attachment of coupling member elements. Hinge portion 195 allows movement of the stabilization members 162, 180 relative to one another in response to motion of the stabilization vertebral level or levels. The lateral offset provided by coupling member 194 allows application of stabilization members 162, 180 in anatomical locations where alignment of axes 163, 181 would not be optimal. Engaging members 192, 193 are positionable in first trans-axial bore 198 and second trans-axial bore 199, respectively, and engageable to respective ones of the end portions 166, 202 to contact the aligned contact portions 168, 204 to prevent stabilization members 162, 180 from disengaging from coupling member 194.

While some of the stabilization systems described and illustrated herein employ threading to connect the respective spinal stabilization members with the coupling member, it is contemplated that the flexible coupling members contemplated herein include other structures to engage with and interconnect the spinal stabilization members. For example, in one non-illustrated form, the spinal stabilization members may engage with the flexible coupling member through a friction or press fit, a ball and socket coupling, or a slot and key arrangement, just to name a few possibilities. In another non-illustrated form, when the flexible coupling member is composed of a polymer material, such as for example, polyethylene, each of the respective spinal stabilization members may include a barbed end structured to engage with the coupling member. Still, other arrangements for coupling the spinal stabilization members with the flexible coupling members are contemplated.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

What is claimed is:

1. A spinal stabilization system, comprising:
    a first elongated stabilization member extending along a longitudinal axis between a first end and an opposite second end;
    a second elongated stabilization member extending along a longitudinal axis between a first end and an opposite second end; and
    a coupling member extending between a first end and an opposite second end, the coupling member including at least a deformable hinge portion disposed between first and second body portions of the coupling member, the coupling member including at least a first receptacle for receiving the first end of the first stabilization member and a second receptacle for receiving the second end of the second stabilization member so the first and second stabilization members are engaged in end-to-end relationship with the first stabilization member extending in a first direction away from the coupling member and the second stabilization member extending in a second direction away from the coupling member, wherein the second direction is generally opposite the first direction, wherein the deformable hinge portion forms a groove in the coupling member that defines a width between the first and second body portions, the groove including a bottom surface connecting the first and second body portions with the bottom surface recessed at a depth below adjacent exterior surfaces of the first and second body portions so that a cross-section of the coupling member through the deformable hinge portion is smaller than cross-sections of the first and second body portions adjacent to the groove.

2. The spinal stabilization system of claim 1, wherein the groove of the deformable hinge portion extends at least partially about an exterior surface of the coupling member and between the first and second body portions.

3. The spinal stabilization system of claim 1, wherein the deformable hinge portion includes a stem extending along said groove between the first and second body portions of the coupling member that is structured to flex in response to normal spinal motion when the first and second stabilization members are secured along a spinal column, wherein the width and depth of the groove is sized so that the first and second body portions of the coupling member contact one another to limit motion of the spinal column when the coupling member is flexed about the stem.

4. The spinal stabilization system of claim 1, wherein the first and second receptacles each extend from an opening thereof at a respective one of the first and second ends of the coupling member into the coupling member from the respective first and second ends of the coupling member in a direction substantially parallel to one another.

5. The spinal stabilization system of claim 4, wherein the first and second receptacles are spaced apart and extend substantially parallel to one another on opposite sides of the coupling member.

6. The spinal stabilization system of claim 5, wherein the first and second receptacles extend beside the hinge portion along opposite sides of the hinge portion.

7. The spinal stabilization system of claim 6, wherein the first and second receptacles each extend between and open at both of the first and second ends of the coupling in member.

8. The spinal stabilization system of claim 1, wherein the first and second receptacles extend from an opening thereof at a respective one of the first and second ends of the coupling member into the coupling member and are in axial alignment with each other.

9. The spinal stabilization system of claim 8, wherein the deformable hinge portion is positioned between ends of the first and second receptacles.

10. The spinal stabilization system of claim 1, wherein the first end of the first stabilization member and the second end of the second elongated stabilization member each include an externally threaded profile structured to threadingly engage with an internally threaded section of respective ones of the first and second receptacles of the coupling member.

11. The spinal stabilization system of claim 10, wherein the externally threaded profiles of the first and second stabilization members each include a contact surface along at least one side thereof and wherein the coupling member further includes first and second trans-axial bores in transverse communication with respective ones of the first and second receptacles such that when the first and second stabilization members are coupled with the coupling member the contact surfaces of the externally threaded profiles are aligned with respective ones of the first and second trans-axial bores and engageable by engaging members received in respective ones of the first and second trans-axial bores to maintain the first and second stabilization members in position relative to the coupling member.

12. The spinal stabilization system of claim 11, wherein the engaging members are externally threaded set screws structured to threadingly mate with an internally threaded portion of the first and second trans-axial bores to be threadingly advanced into contact with the contact surfaces of the first and second coupling bodies of the first and second elongated stabilization members.

13. The spinal stabilization system of claim 1, wherein the first and second elongated stabilization members each include a member portion extending from the coupling member, the member portions each having a cross-section with a diameter.

14. The spinal stabilization system of claim 13, wherein the diameters of the member portions are the same.

15. The spinal stabilization system of claim 13, wherein the diameter of one of the member portions is less than the diameter of the other member portion.

16. The spinal stabilization system of claim 1, wherein the deformable hinge portion is integrally formed with and extends between the first and second body portions of the coupling member.

17. The spinal stabilization system of claim 1, wherein the coupling member extends along a longitudinal axis between the first and second ends thereof and the groove extends transversely to the longitudinal axis.

18. The spinal stabilization system of claim 17, wherein the groove extends completely around the coupling member.

19. The spinal stabilization system of claim 17, wherein the first and second body portions are concentric relative to the longitudinal axis and the deformable hinge portion is eccentrically positioned between the first and second body portions.

20. The spinal stabilization system of claim 19, wherein the groove extends around only a portion of the coupling member.

21. The spinal stabilization system of claim 1, wherein the first and second spinal stabilization members are comprised of a first material and the coupling member is comprised of a different material than the first and second spinal stabilization members.

22. A spinal stabilization system, comprising:
a first elongated stabilization member extending along a longitudinal axis between a first end and an opposite second end:
a second elongated stabilization extending along a longitudinal axis between a first end and an opposite second end:
a coupling member with a body extending from a first end to a second end, the body including opposite side walls extending between the first and second ends, wherein the coupling member includes:
a first receptacle extending into the body from the first end and being structured for engagement with one of the first and second ends of the first elongate spinal stabilization member and a second receptacle extending into the body from the second end and being structured for engagement with one of the first and second ends of the second elongate spinal stabilization member so the first and second stabilization members are engaged in end-to-end relationship, the first and second receptacles being situated such that the first spinal stabilization member extends in a first direction from the body and the second spinal stabilization member extends in a second direction from the body that is opposite the first direction; and
at least one deformable hinge portion disposed between the first and second ends of the body, wherein the at least one deformable hinge portion is structured to provide movement of at least one of the first and second ends of the body relative to the other of the first and second ends of the body in response to motion of a spinal column of a patient when the coupling member is implanted along the spinal column with the first and second stabilization members, wherein the deformable hinge portion forms a groove in the coupling member that defines a width between first and second body portions of the body of the coupling member, the groove including a bottom surface connecting the first and second body portions with the bottom surface recessed at a depth below adjacent exterior surfaces of the first and second body portions so that a cross-section of the coupling member through the deformable hinge portion is smaller than cross-sections of the first and second body portions adjacent to the groove.

23. The spinal stabilization system of claim 22, wherein the deformable hinge portion extends between and is integrally formed with the first and second body portions of the body of the coupling member.

24. The spinal stabilization system of claim 23, wherein the first body portion extends from the first end of the body to the deformable hinge portion, and the second body portion extends from the second end of the body to the hinge portion.

25. The spinal stabilization system of claim 22, wherein the first and second receptacles extend from an opening thereof at a respective one of the first and second ends of the coupling member and are substantially parallel to one another.

26. The spinal stabilization system of claim 25, wherein the first and second receptacles are spaced apart from one another on opposite sides of a central axis of the body of the coupling member extending between the first and second ends of the body.

27. The spinal stabilization system of claim 26, wherein each the first and second receptacles open at both the first and second ends of the body of the coupling member.

28. The spinal stabilization system of claim 22 wherein the first and second receptacles extend from an opening thereof at a respective one of the first and second ends of the coupling member into the coupling member and are in axial alignment with one another.

29. The spinal stabilization system of claim 22, wherein the body of the coupling member further includes first and second trans-axial bores communicating in a transverse arrangement with respective ones of the first and second receptacles, the first and second trans-axial bores being structured to receive an engaging member therein.

30. The spinal stabilization system of claim 29, wherein the first and second trans-axial bores include internal threading.

31. The spinal stabilization system of claim 29, wherein the first and second receptacles of the body of the coupling member include internal threading for engaging the respective first and second spinal stabilization members when positioned therein.

32. The spinal stabilization system of claim 22, wherein the deformable hinge portion extends between and is integrally formed with the first and second body portions of the coupling member and wherein the first body portion extends between the first and second ends of the body along one of the opposite side walls and the second body portion extends between the first and second ends of the body along the other of the opposite side walls.

33. The spinal stabilization system of claim 22, wherein the deformable hinge portion includes a stem extending along the groove and connecting the first and second body portions of the coupling member, the deformable hinge portion being structured to flex in response to normal spinal motion when the first and second stabilization members are secured along a spinal column, wherein the width and depth of the groove is sized so that the first and second body portions of the coupling member contact one another when the coupling member is flexed about the stem to limit motion of the spinal column.

* * * * *